United States Patent [19]

Kursewicz et al.

[11] Patent Number: 4,463,209

[45] Date of Patent: Jul. 31, 1984

[54] AROMATICS PROCESSING

[75] Inventors: Christine H. Kursewicz, Haddonfield; John P. McWilliams, Woodbury, both of N.J.

[73] Assignee: Mobil Oil Corporation, New York, N.Y.

[21] Appl. No.: 533,618

[22] Filed: Sep. 19, 1983

Related U.S. Application Data

[63] Continuation of Ser. No. 121,340, Feb. 14, 1980, abandoned.

[51] Int. Cl.³ .......................... C07C 2/86; C07C 5/22; C07C 4/12
[52] U.S. Cl. .................................... 585/467; 585/470; 585/475; 585/474; 585/481; 585/486; 502/51
[58] Field of Search ............... 585/467, 470, 474, 475, 585/481, 486; 502/51

[56] References Cited

U.S. PATENT DOCUMENTS 3,751,504 8/1973 Keown et al. ...................... 585/467
3,907,663 9/1975 Owen ................................. 585/467

Primary Examiner—Curtis R. Davis
Attorney, Agent, or Firm—Alexander J. McKillop; Michael G. Gilman; Dennis P. Santini

[57] ABSTRACT

Improved aromatic conversion processes are provided by novel regeneration techniques. Aromatic processes that would benefit from this invention include those processes using catalysts comprising zeolites having a silica to alumina mole ratio of at least about 12 and a constraint index within the approximate range of 1 to 12 and which require regeneration to burn off coke from said catalysts. The improvement of the instant invention resides in conducting said regeneration in the presence of steam under controlled conditions to enhance the activity of the catalysts.

17 Claims, 1 Drawing Figure

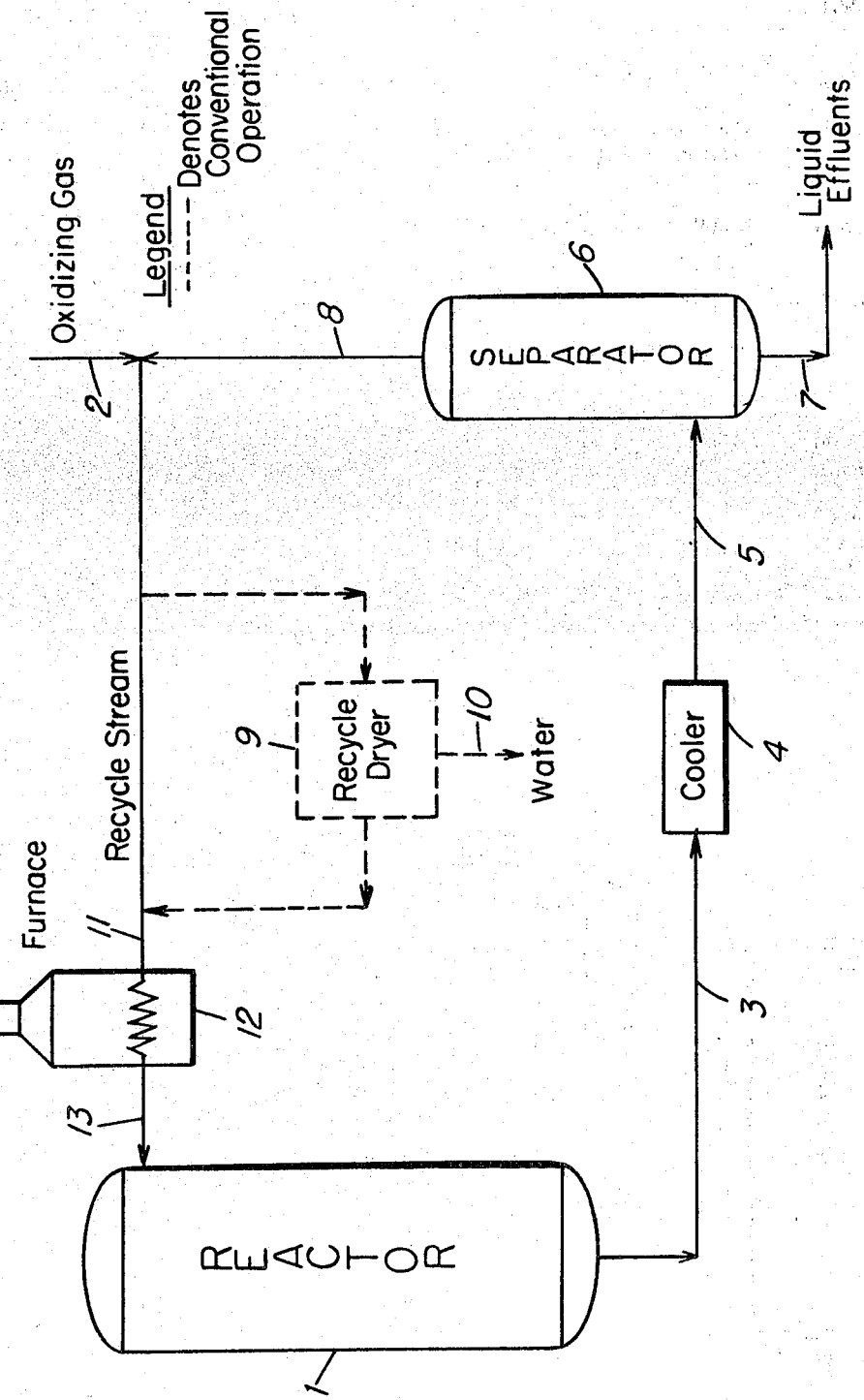

4,463,209

AROMATICS PROCESSING

This is a continuation of copending application Ser. No. 121,340, filed on Feb. 14, 1980, now abandoned.

BACKGROUND OF THE INVENTION

1. Field of the Invention

This invention relates to improved aromatics processing. More particularly, this invention is concerned with regenerating aromatics processing catalysts in the presence of steam in such a manner as to enhance their catalytic activities.

2. Description of the Prior Art

U.S. Pat. Nos. 3,126,422; 3,413,374; 3,598,878; 3,598,879 and 3,607,961 show vapor-phase disproportionation of toluene over various catalysts.

The disproportionation of aromatic hydrocarbons in the presence of zeolite catalysts has been described by Grandio et al. in the Oil and Gas Journal, Vol. 69, Number 48(1971).

The use of a catalyst comprising a crystalline zeolite characterized by a silica to alumina mole ratio of at least about 12 and a constraint index within the approximate range of 1 to 12 for the disproportionation of toluene is described in many patents, such as U.S. Pat. Nos. 4,011,276, 4,016,219, 4,052,476, 4,097,543, and 4,098,837, just to name a few.

Since the announcement of the first commercial installation of Octafining in Japan in June, 1958, this process has been widely installed for the supply of p-xylene. See "Advances in Petroleum Chemistry and Refining", volume 4 page 433 (Interscience Publishers, New York 10061). Demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./U.S. Gal. |
|---|---|---|---|
| Ethyl benzene | −139.0 | 277.0 | 7.26 |
| P—xylene | 55.9 | 281.0 | 7.21 |
| M—xylene | −54.2 | 282.4 | 7.23 |
| O—xylene | −13.3 | 292.0 | 7.37 |

Principal sources of $C_8$ aromatics are catalytically reformed naphthas and pyrolysis distillates. The $C_8$ aromatic fractions from these sources vary quite widely in composition but are usually in the range 10 to 32 wt % ethyl benzene with the balance, xylenes, being divided approximately 50 wt % meta, and 25 wt % each of para and ortho.

Individual isomer products may be separated from the naturally occurring mixtures by appropriate physical methods. Ethyl benzene may be separated by fractional distillation, although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes.

The Octafining process operates in conjunction with the product xylene or xylenes separation processes. A virgin $C_8$ aromatics mixture is fed to a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer. As in reforming, the catalyst contains a small amount of platinum and the reaction is carried out in a hydrogen atmosphere.

Under recommended design conditions, a considerable volume of hydrogen is introduced with the $C_8$ aromatics. In order to increase throughput, there is great incentive to reduce hydrogen circulation with consequent increase in aging rate of the catalyst. Aging of catalyst occurs through deposition of carbonaceous materials on the catalyst, with need to regenerate by burning off the coke when the activity of the catalyst has decreased to an undesirable level. Typically the recommended design operation will be started up at about 850° F. with reaction temperature being increased as needed to maintain the desired level of isomerization until reaction temperature reaches about 900° F. At that point the isomerizer is taken off stream and regenerated by burning of the coke deposit.

During regeneration, burning proceeds very slowly with diluted oxidizer medium in order to minimize damage to the catalyst. The several days required for regeneration are non-productive and the catalyst after regeneration is at a reduced activity level. For example, an operation at a hydrogen to hydrocarbon recycle ratio of 6.5 results in a cycle life of about 3 months between regenerations with replacement of the catalyst required after about 1 year, four cycles.

In a typical plant for utilization of Octafining, a mixture of $C_8$ aromatics is introduced to an ethyl benzene tower wherein the stream is stripped of a portion of its ethyl benzene content, to an extent consistent with retaining all the xylenes in the feed stream without unduly expensive "superfractionation". Ethyl benzene is taken overhead while a bottom stream, consisting principally of xylenes, together with a significant amount of ethyl benzene, passes to a xylene splitter column. The bottoms from the xylene splitter constituted by o-xylene and $C_8$ aromatics passes to the o-xylene tower from which o-xylene is taken overhead and heavy ends are removed. The overhead from the xylene splitter column is transferred to conventional crystallization separation. The crystallizer operates in the manner described in Machell et al., U.S. Pat. No. 3,662,013 dated May 9, 1972.

Because its melting point is much higher than that of the other $C_8$ aromatics, p-xylene is readily separated in the crystallizer after refrigeration of the stream and a xylene mixture lean in p-xylene is transferred to an isomerization unit. The isomerization charge passes through a heater, is admixed with hydrogen and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product constituted by $C_8+$ hydrocarbons is recycled in the system to the inlet of the xylene splitter.

It will be seen that the system is adapted to produce maximum quantities of p-xylene from a mixed $C_8$ aromatic feed containing all of the xylene isomers plus ethyl benzene. The key to efficient operation for that purpose is in the isomerizer which takes crystallizer effluent lean in p-xylene and converts the other xylene isomers in part to p-xylene for further recovery at the crystallizer.

The Octafining process has been extensively discussed in the literature, for example:

1. Pitts, O. M., Connor, J. E. Leun, L. M., *Ind. Eng. Chem.*, 47, 770 (1955).
2. Fowle, M. J., Bent, R. D., Milner, B. E., presented at the Fourth World Petroleum Congress, Rome, Italy, June 1955.
3. Ciapetta, F. G., U.S. Pat. No. 2,550,531 (1951).
4. Ciapetta, F. G., and Buck, W. H., U.S. Pat. No. 2,589,189.
5. Octafining Process, Process Issue, Petroleum Refinery, 1st Vol. 38 (1959), No. 11, Nov., p. 278.

A typical charge to the isomerizing reactor (effluent of the crystallizer) may contain 17 wt. % ethyl benzene, 65 wt. % m-xylene, 11 wt % p-xylene and 7 wt. % o-xylene. The thermodynamic equilibrium varies slightly with temperature. The objective in the isomerization reactor is to bring the charge as near to theoretical equilibrium concentrations as may be feasibly consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethane and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has a very small effect on ethyl benzene approach to equilibrium.

Concurrent loss of ethyl benzene to other molecular weight products relates to % approach to equilibrium. Products formed from ethyl benzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, benzene, toluene, $C_9+$ aromatics and $C_5$ and lighter hydrocracking products.

Ethyl benzene has been found responsible for a relatively rapid decline in catalyst activity and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

Another xylene isomerization which has achieved widespread commercial use is low pressure operation in vapor phase. Temperatures employed are in the same range as for Octafining, in the neighborhood of 850° F. Pressures are only that required to equal pressure drop through the downstream recovery towers, heat exchangers and the like. For all practical purposes, this is an atmospheric pressure reaction with reactor inlet pressure of about 30 pounds per square inch, gauge. The catalyst is essentially silica-alumina, the acid amorphous heterogeneous catalyst employed in a number of such acid catalyzed processes. Several advantages for that type of isomerization will be immediately apparent.

The unit cost of catalyst is drastically reduced by omission of platinum. At these low pressures, the reactor vessels are made of inexpensive steel and need no structural provision for resisting pressure stress. The process is practical without introduction of molecular hydrogen and needs no auxiliaries for manufacture and recycle of that gas. These features greatly reduce capital and operating costs and have made the low pressure process essentially competitive with Octafining despite the requirement for large vessels at low pressure and low space velocity and the operating disadvantages inherent in the process.

A primary drawback of low pressure vapor phase isomerization as practiced heretofore is its low tolerance for ethyl benzene in the charge. The catalyst will convert ethyl benzene only at high severities such that unacceptable loss of xylene occurs by disproportionation.

Low pressure isomerization as practiced heretofore accepts a further disadvantage in that the catalyst rapidly declines in activity due to deposition of "coke", a carbonaceous layer masking the active sites of the porous silica-alumina catalyst presently conventional in this operation. The coke can be removed by burning with air to regenerate the activity of the catalyst. Continuity of operation is achieved by the well-known "swing reactor" technique. In this technique, two or more reactors are employed, one of which is on stream, while burning regeneration is conducted on a reactor containing spent catalyst which has lost activity by coke deposition. Cycles of two to four days are common practice using one reactor on stream for that period and then shifting to a freshly regenerated vessel.

Present commercial practice involves many large plants of both the Octafining and low pressure types in a loop of p-xylene separation and recycle of other isomers, together with such quantity of ethyl benzene as may be present, through isomerization and back to p-xylene recovery. The commercial options presently in use are Octafining at high pressure with large quantities of hydrogen or low pressure (essentially atmospheric) isomerization with complicated cycling of a swing reactor and necessity for expensive distillation to remove ethyl benzene from the charge to some acceptable level, usually about 5%.

A further alternative heretofore described is isomerization in liquid phase at a pressure adequate to maintain that phase. Highly active zeolite catalysts are effective under these conditions and demonstrate long cycle life, possibly because precursors of coke are dissolved by the reactant liquid and flushed from the reactor before deterioration to coke. See, for example, Wise, U.S. Pat. No.

3,377,400; Bowes et al., U.S. Pat. No. 3,578,723; and Haag et al., U.S. Pat. No. 3,856,871.

It is further known that zeolites characterized by having a silica to alumina mole ratios of at least 12 and constraint indices within the approximate range of 1 to 12 are very effective as catalysts for the isomerization of xylenes. See Burress, U.S. Pat. No. 3,856,873, Morrison, U.S. Pat. No. 3,856,872; Haag et al., supra; Hayward, U.S. Pat. No. 3,856 874; Mitchell et al., U.S. Pat. No. 4,101,596; Olson et al., U.S. Pat. No. 4,159,282; Nicoletti et al., U.S. Pat. No. 4,159,283; and Tabak et al., U.S. Pat. No. 4,163,028. In the absence of hydrogen, these zeolites accumulate coke on stream in the manner to be expected from knowledge in the art to require short cycle times, when operating outside the bounds of limits now found essential to prolonged on-stream periods.

It is known in the art that the use of steam (water) and/or ammonia can be utilized to modify the activity of acid catalysts, e.g. clays, silica-aluminas and zeolites. Much of the emphasis in the field of catalyst activity modification has been directed towards reducing the activity of catalysts. For example, U.S. Pat. No. 4,016,218 teaches the use reduction of catalytic activity of a class of zeolites having a silica to alumina mole ratio of at least 12 and a constraint index within the approximate range of 1 to 12 by the use of prior thermal treatment. Such prior thermal treatment includes the use of a steam atmosphere.

Hydrogen zeolites of the 1 to 12 constraint index type are generally prepared from their alkyl ammonium and ammonium form precursors by calcining in an inert atmosphere, usually in nitrogen at about 1000° F. The more costly nitrogen atmosphere is chosen over the cheaper heating in air to avoid temperature runaway and steam formation that is known to damage the catalyst and results in lower activity. Small samples in the laboratory can be calcined in air without significant steam damage if the temperature is controlled by a slow heat up and by allowing any steam formed to diffuse away. With this careful first calcination, hydrogen zeolites result that are free of residual nitrogen compounds and have the maximum number of acidic hydroxyl group, which is equal to the number of framework aluminums. Samples thusly prepared are designated "fresh samples". The corresponding catalytic activity of these fresh samples is called "initial activity" and when measured by the alpha ($\alpha$) test as described hereinafter, assigned the designation of "$\alpha$."

It has long been known that the catalytic activity of hydrogen zeolites can be reduced by high temperature heating and especially by steaming.

It is also known that the deactivation due to steam is more pronounced at higher temperatures and longer reaction times. It is also more pronounced at higher steam pressures. Deactivation in the absence of steam, i.e., in an inert atmosphere, requires more severe conditions than steam deactivation.

Recently it has been found that the use of water can be employed to improve certain zeolite catalyst characteristics, while maintaining catalyst activity levels. U.S. Pat. Nos. 4,149,960 and 4,150,062 describe the use of about 0.5 to about 15 moles of water per mole of feedstock in order to substantially reduce the coking and aging rates of the zeolite catalysts used in the processes of these disclosures.

U.S. Pat. Nos. 3,493,519 teaches a method of using steam for the stabilization of Y-faujasite zeolite. There, a chelating agent was used after steaming to take out the excess aluminum from the zeolite. The resultant catalyst of this process is a hydrothermally stable zeolite catalyst having high hydrocarbon conversion activity.

In U.S. Pat. Nos. 3,546,100, it is disclosed that a rare earth exchanged zeolite hydrocracking catalyst such as zeolites X or Y can be improved with respect to its cracking activity and selectivity by using water in controlled amounts to activate catalyst cracking sites. This disclosure states that the amount of water be maintained during the process such that the water vapor partial pressure is kept at a level of about 10 to about 130 mm. water vapor.

SUMMARY OF THE INVENTION

In accordance with the present invention, there has now been discovered improved aromatics conversion processes which utilize catalysts comprising zeolites which are characterized by a silica to alumina mole ratio of at least about 12 and a constraint index, as defined hereinafter, within the approximate range of 1 to 12. The improvement resides in regenerating said catalysts, in air in the presence of steam under controlled conditions. Whereas, the prior art taught that steam and high temperatures like those encountered during regeneration to burn off coke were detrimental to zeolite structure and catalytic activity, the present invention takes advantage of the presence of steam. The prior art aromatic processes taught the use of recycle gas driers to minimize exposure of the zeolite containing catalyst to water vapor formed during regeneration. In direct contradiction to the prior art teachings, recycle gas driers are expressly not utilized in the improved processes of the instant invention.

By regenerating said catalysts in the presence of steam at partial pressures of between about 0.1 psia and about 4.0 psia, at a contact time of between about 12 hours and about 72 hours and at a temperature of between about 750° F. and about 900° F., catalytic activity can be enhanced many times greater than the initial activity. The enhanced catalyst activity attained in accordance with the present invention could translate to longer cycle lengths and possibly ultimate catalyst fill life in aromatic processes such as isomerization, disproportionation, alkylation, transalkylation, dealkylation, cracking, etc.

DESCRIPTION OF THE DRAWING

The drawing is a typical aromatics process regeneration scheme.

DESCRIPTION OF PREFERRED EMBODIMENTS

The zeolite catalysts herein described are members of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e, high silica to alumina mole ratios, they are very active even when the silica to alumina mole ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of silicon atoms interconnected by oxygen. It is to be understood, of course, that these rings are those formed by the regular disposition of the tetrahedra making up anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intercrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character may be advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2.0 |
| Clinoptilolite | 3.4 |
| TMA Offretite | 3.7 |
| Beta | 0.6 |
| ZSM-4 | 0.5 |
| H—Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratios. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-23, ZSM-35 and ZSM-38 and other similar materials. U.S. Pat. Nos. 3,702,886 describing and claiming ZSM-5 is incorporated herein by reference.

ZSM-11 is more particularly described in U.S. Pat. Nos. 3,709,979, the entire contents of which is incorporated herein by reference.

ZSM-12 is more particularly described in U.S. Pat. Nos. 3,832,449, the entire contents of which is incorporated herein by reference.

ZSM-23 is more particularly described in U.S. Pat. No. 4,076,842, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite; however, the presence of these cations does appear to favor the formation of this special type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations Natural minerals which may be so treated include ferrierite, brewsterite, stilbite, dachiardite, epistilbite, heulandite, and clinoptilolite. The preferred cystalline zeolites are ZSM-5, ZSM-11, ZSM-12, ZSM-23, ZSM-35 and ZSM-38, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves", London, April 1967, published by the Society of Chemical Industry, London, 1968. When the crystal structure is unknown, the crystal framework density may be determined by classical pycnometer techniques.

For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5 -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |

When synthesized in the alkali metal form, the zeolite is conveniently converted to the hydrogen form, generally by intermediate formation of the ammonium form as a result of ammonium ion exchange and calcination of ammonium form to yield the hydrogen form. In addition, to the hydrogen form, other forms of the zeolite wherein the original alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

In practicing the desired method, it may be desirable to incorporate the above-described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaoline families, which families include the sub-bentonites and the kaolins commonly known as Dixie, McNamee-Georgia and Florida clays or others in which the mineral constituent is halloysite, kaolinite, dickite, nacrite or anauxite. Such clays can be used in a raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The degree of zeolite catalyst activity can be measured and compared by means of "alpha value" ($\alpha$). The alpha value reflects the relative activity of the catalyst with respect to a high activity silica-alumina cracking catalyst. To determine the alpha value as such term is used herein, n-hexane conversion is determined at about 800° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and the remainder $SiO_2$. This method of determining alpha, modified as described above, is more fully described in the *Journal of Catalysis,* Vol. VI, pages 278-287, 1966.

One measure of comparison used to relate catalyst activities is "relative activity". Relative activity is the ratio of the activity of the catalyst after regeneration over the initial activity. Thus relative activity can be expressed as follows:

Relative Activity $= \alpha/\alpha_o$.

The relative activity of a catalyst at the point of initial activity is therefore 1 since $\alpha/\alpha_o = \alpha_o/\alpha_o = 1$.

The feedstock employed in the present invention comprises aromatic compounds, such as benzene, toluene and xylene, to name a few. The particular feedstock employed depends on the aromatic process being conducted. Thus for xylene isomerization, the feedstock would generally be a stream of $C_8$ aromatics of reduced p-xylene content, while the chargestock in a disproportionation process would be predominantly toluene.

Conversion conditions for conducting an isomerization process in accordance with this invention include temperatures of between about 500° F. and 1000° F., a pressure of between about atmospheric and 1,000 psig and a weight hourly space velocity of between about 0.5 and 250.

Conversion conditions for the undertaking of a toluene disproportionation process in accordance with this invention include a temperature of between about 400° F. and 1400° F., a pressure of between about atmospheric and 1,000 psig and a weight hourly space velocity of between about 0.1 and 20. When the conversion is alkylation by the present process, conversion conditions include a temperature of between about 100° F. and 950° F., a pressure of between about 25 and 800 psig and a weight hourly space velocity of between about 1 and 20.

When the conversion is transalkylation by the instant process, conversion conditions include a temperature of between about 650° F. and 1100° F., a pressure of between about 25 and 800 psig and a weight hourly space velocity of between about 1 and 20.

Further, when the conversion by the present process is cracking, catalytic conversion conditions should be maintained within certain ranges, including a temperature of from about 700° F. to about 1200° F., preferably from about 800° F. to about 1000° F., a pressure of from about atmospheric to about 200 psig, a WHSV (when a flow operation) of from about 0.5 $hr^{-1}$ to about 50 $hr^{-1}$, preferably from about 1 $hr^{-1}$ to about 10 $hr^{-1}$, and a contact time (when a batch operation) of from about 0.01 hour to about 24 hours, preferably from about 0.1 hour to about 10 hours.

The aromatic processes as encompassed by this invention may be conducted in either batch or fluid bed operation with attendant benefits of either operation readily obtainable.

The improvement involved in the present invention comes about during the regeneration cycle of the aforementioned aromatic processes. Such regeneration is necessary to burn off the carbonaceous materials (coke) which deposit on the catalyst particles.

Since it was known in the prior art that the presence of steam deactivates catalysts, especially zeolite catalysts, regeneration cycles in aromatic processes were undertaken so as to limit the amount of steam present to the lowest possible levels. It was found that loss in activity caused by steaming during regeneration was cumulative and the effect tended to snowball; shorter cycles led to more frequent regenerations, which resulted in further steaming and deactivation. To this end, prior art aromatic processes contained regeneration systems which included recycle dryers to reject any water vapor formed during the combustive regeneration process. The present invention teaches the exclusion of such recycle dryers and the control of conditions during regeneration to mildly steam the catalysts so as to enhance their activity, rather than to deactivate them. Regeneration systems must be maintained to expose the catalysts to a partial pressure of water in the range between about 0.1 psia and 4.0 psia, more preferably between about 1.0 psia and 2.0 psia for a period of time of between about 12 hours and 72 hours, more preferably between about 24 hours and 48 hours.

A conventional aromatics process regeneration scheme is set forth in the flowsheet in the annexed drawing. The reactor 1 contains coked zeolite catalyst as described herein. In order to burn off the deposited coke which is deposited on said catalysts, oxidizing gas enters the system through line 2. Such oxidizing gas comprises oxygen, e.g. air containing nitrogen, oxygen and water vapor. The oxidizing gas reacts with the coke to form a hot combustion gas stream. This hot gas stream exits the reactor 1 via line 3 and is cooled in a cooler 4. Cooled gases exit the cooler 4 and enter the separator 6 through line 5. Liquid effluents exit the separator 6 through line 7. Gaseous effluent containing water vapor leaves the separator in line 8. A typical gaseous effluent during regeneration would comprise $N_2$, $O_2$, $H_2O$, CO, and $CO_2$. During regeneration in the prior art processes, i.e. during conventional operation, a recycle dryer 9 would eliminate water from the gaseous effluent cyclically via line 10 and return a recycle gas with a small amount of water vapor back to the reactor through line 11. The recycle stream including both the gaseous effluent from the separator 6 and the oxidizing gas are heated in a furnace 12 and the thusly heated recycle stream enters the reactor 1 via conduit 13. In conducting regeneration in accordance with the present invention, the recycle dryer would be eliminated with steam containing gases being recycled back to the furnace and reactor.

In a particular embodiment of the present invention, the reactor during regeneration would operate at a temperature of between about 750° F. and 1000° F., with the separator operating at a temperature of between about 35° F. and 150° F., more particularly between about 60° F. and 150° F. Without the use of a recycle dryer, the partial pressure of water in this system during regeneration would be maintained between about 0.25 and 3.7 psia with the catalyst being contacted at these regeneration conditions.

The following examples will serve to illustrate the present invention without limiting same.

EXAMPLE 1

HZSM-5 was prepared according to the following procedure:

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W.R. Grace Chemical Division). The solution was cooled to approximately 15° C.

An acid solution was prepared by adding 1 part aluminum sulfate (17.2 wt % $Al_2O_3$) to 16.4 parts water followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:

$SiO_2/Al_2O_3 = 78.4$
$Na_2O/Al_2O_3 = 49.9$

An organic solution was prepared by adding 1.6 parts n-propyl bromide and 3.1 parts methyl ethyl ketone to 1.9 parts tri-n-propylamine.

After the gel was heated to about 95° C., agitation was reduced and the organic solution was added above the gel. This mixture was held at about 95°–110° C. for 14 hours, then severe agitation was resumed. When approximately 65% of the gel was crystallized, the temperature was incrased to 150°–160° C. and held there until crystallization was complete. Unreacted organics were removed by flashing and the remaining contents cooled.

The zeolite slurry product was diluted with 4–5 parts water per part slurry and 0.002 parts of flocculent (Rohm & Haas Primafloc C-7) per part slurry, allowed to settle and supernatant liquid was drawn off. The settled solids were reslurried to the original volume of the preceding step with water and 0.00005 parts of flocculant per part slurry. After settling, the aqueous phase was decanted. This procedure was repeated until the sodium level of the zeolite was less than 1.0 wt %. The washed zeolite was then filtered, dried and identified as ZSM-5 having a silica/alumina mole ratio of at least 12; i.e., about 70, and a constraint index of between 1 and 12; i.e., about 8.3.

The dried zeolite was then mixed with alumina and water. It was then extruded into pellets and dried. The extruded material contained 65 parts ZSM-5 per 35 parts alumina.

The dried extrudate was calcined for three hours at 538° C. in flowing nitrogen. After cooling, the extrudate was contacted with an ammonium nitrate exchange solution for one hour at ambient temperature. This exchange was then repeated until the sodium level was less than 0.05 wt %. After this exchange, the extrudate was washed, dried and calcined in a nitrogen containing gas at 538° C. for about 3 to 6 hours.

EXAMPLES 2–4

The catalyst prepared according to Example 1 was steamed at various conditions of time, temperature and steam partial pressure. Examples 2 and 3 illustrate how conventional steaming decreases catalytic activity, while Example 4 shows how steaming according to the present invention brings forth a substantial increase in catalytic activity. The measurement for catalytic activity used in all these examples is in terms of "alpha value" with the nominal fresh alpha value ($\alpha$) of the catalyst at 136. The steaming results for Examples 2–4 are shown in Table 1.

TABLE 1

| | STEAMING CONDITIONS | | | |
|---|---|---|---|---|
| Example No. | Time, Hrs. | Temperature, °F. | Steam Partial Pressure Psia | $\frac{\alpha}{\alpha_o}$ |
| 2 | 3 | 1000 | 14 | 0.2 |
| 3 | 2.5 | 900 | 14.7 | 0.7 |
| 4 | 60 | 850 | 1.7 | 3 |

EXAMPLES 5–6

These examples demonstrate how a catalyst regenerated according to the process of the instant invention can dramatically improve catalytic activity in a xylene isomerization process. The catalyst for these examples is regenerated according to Example 4 with the separator operating at 120° F. The results for Examples 5 and 6 are given in Table 2.

The first and second cycles cited in Table 2 refer respectively to operation before regeneration and operation after regeneration. The improvement in xylene isomerization using the process of this invention is readily seen by the gain in Δ Activity in both Examples 5 and 6. The expression "Δ Activity" means that the same conversion can be achieved at a lower temperature. Thus in Example 5, a temperature of 13° lower could be used and in Example 6, a temperature of 21° F. lower could be utilized.

TABLE 2

| | Example 5 | | Example 6 | |
|---|---|---|---|---|
| | 1st Cycle | 2nd Cycle | 1st Cycle | 2nd Cycle |
| PROCESS OPERATING CONDITIONS | | | | |
| Pressure, Psig | 25 | 25 | 25 | 25 |
| WHSV | 5 | 5 | 5 | 5 |
| Temperature, °F. | 552 | 547 | 602 | 597 |
| Time on Stream, Days | 2.6 | 2.5 | 5.6 | 6.5 |
| CONVERSIONS | | | | |
| Ethylbenzene Conversion, (EBC) Wt. % | 8.4 | 11.3 | 25.9 | 31.9 |
| P—Xylene Equil., Approach % | 103.2 | 101.6 | 102.2 | 101.9 |
| O—Xylene Equil., Approach % | 84.2 | 89.5 | 92.1 | 92.0 |
| Xylene loss, Wt. % (XL) | 0.7 | 1.5 | 2.7 | 3.6 |
| XL/EBC | 0.08 | 0.13 | 0.10 | 0.1 |
| Δ ACTIVITY, °F. | — | 13 | — | 21 |
| REGENERATION CONDITIONS | | | | |
| Average Reactor Temperature, °F. | | 850 | | 850 |
| Reactor Pressure, Psig | | 100 | | 100 |

TABLE 2-continued

|  | Example 5 | | Example 6 | |
| --- | --- | --- | --- | --- |
|  | 1st Cycle | 2nd Cycle | 1st Cycle | 2nd Cycle |
| Separator Temperature, °F. | 120 | | 120 | |
| Water Partial Pressure, Psia | 1.7 | | 1.7 | |
| Approximate Contact Time, Hours | 60 | | 60 | |

What is claimed is:

1. In a process for the conversion of aromatic containing feedstocks in which said feedstocks are contacted in a reactor vessel, under conversion conditions, with a catalyst comprising a zeolite having a silica to alumina mole ratio of at least 12 and a constraint index within the approximate range of 1 to 12, and which includes a regeneration step to burn off carbonaceous materials which deposit on said catalyst, said regeneration step comprising contacting said catalyst containing carbonaceous materials with oxidizing gas, the improvement which comprises conducting the regeneration step in the presence of steam at controlled regeneration conditions including a steam partial pressure of between about 0.1 psia and about 4.0 psia, a contact time of between about 12 hours and about 72 hours and a temperature of between about 750° F. and about 1000° F.

2. The process of claim 1 wherein the regeneration conditions include a steam partial pressure of between about 1.0 psia and about 2.0 psia, a contact time of between about 24 hours and about 48 hours and a temperature of between about 750° F. and about 1000° F.

3. The process of claim 1 wherein said zeolite is selected from the group consisting of ZSM-5, ZSM-11, ZSM-12, ZSM-23, ZSM-35 and ZSM-38.

4. The process of claim 3 wherein said zeolite is ZSM-5.

5. The process of claim 1 wherein said conversion is isomerization and said conversion conditions include a temperature of between about 500° F. and 1000° F., a pressure of between about atmospheric and 1,000 psig, and a weight hourly space velocity of between about 0.5 and 250.

6. The process of claim 5 wherein said conversion is xylene isomerization.

7. The process of claim 1 wherein said conversion is toluene disproportionation and said conversion conditions include a temperature of between about 400° F. and 1400° F., a pressure of between about atmospheric and 1,000 psig, and a weight hourly space velocity of between about 0.1 and 20.

8. The process of claim 1 wherein said conversion is alkylation and said conversion conditions include a temperature of between about 100° F. and 950° F., a pressure of between about 25 and 800 psig, and a weight hourly space velocity of between about 1 and 20.

9. The process of claim 1 wherein said conversion is transalkylation and said conversion conditions include a temperature of between about 650° F. and 1100° F., a pressure of between about 25 and 800 psig, and a weight hourly space velocity of between about 1 and 20.

10. The process of claim 1 wherein said conversion is cracking and said conversion conditions include a temperature of between about 700° F. and 1200° F., a pressure of between about atmospheric and 200 psig, and a weight hourly space velocity of between about 0.5 and 50.

11. The process of claim 1 wherein the regeneration step further comprises withdrawing a hot combustion stream gas from said reactor through a cooler and separator and returning said gases back to the reactor.

12. The process of claim 11 wherein said hot gas stream contains steam.

13. The process of claim 11 wherein said separator is maintained at a temperature of between about 35° F. and 150° F.

14. The process of claim 11 wherein said separator is maintained at a temperature of between about 60° F. and 150° F.

15. The process of claim 1 wherein said oxidizing gas is oxygen containing mixtures.

16. The process of claim 15 wherein said oxidizing gas is air.

17. The process of claim 1 wherein said steam partial pressure is between about 0.25 psia and about 3.7 psia.

* * * * *